United States Patent [19]
Shenoy et al.

[11] Patent Number: 5,616,689
[45] Date of Patent: Apr. 1, 1997

[54] METHOD OF CONTROLLING STRUCTURE STABILITY OF COLLAGEN FIBERS PRODUCED FORM SOLUTIONS OR DISPERSIONS TREATED WITH SODIUM HYDROXIDE FOR INFECTIOUS AGENT DEACTIVATION

[75] Inventors: Vivek N. Shenoy, Sunnyvale; Timothy T. Revak, Los Altos; George H. Chu, Cupertino; Hugh R. McMullin, Menlo Park; Joel S. Rosenblatt, Palo Alto, all of Calif.; George R. Martin, Bethesda, Md.

[73] Assignee: Collagen Corporation, Palo Alto, Calif.

[21] Appl. No.: 274,673

[22] Filed: Jul. 13, 1994

[51] Int. Cl.$^6$ .............................. A61K 38/17; C07K 1/00
[52] U.S. Cl. ...................... 530/356; 530/402; 530/410; 106/159.1; 106/147.1; 106/155.2; 106/156.2; 106/156.1; 525/54.1
[58] Field of Search .................................... 530/356, 402, 530/410; 514/8, 21, 801; 106/124; 525/54.1

[56] References Cited

U.S. PATENT DOCUMENTS

| | | | |
|---|---|---|---|
| 2,934,446 | 4/1960 | Highberger et al. | 106/155 |
| 3,121,049 | 2/1964 | Nishihara | 195/6 |
| 3,131,130 | 4/1964 | Oneson | 195/6 |
| 3,530,037 | 9/1970 | Nishihara | 195/6 |
| 4,021,522 | 5/1977 | Daniel | 530/356 |
| 4,097,234 | 6/1978 | Sohde et al. | 530/356 |
| 4,233,360 | 11/1980 | Luck et al. | 428/310 |
| 4,511,653 | 4/1985 | Play et al. | 435/69.1 |
| 4,980,403 | 12/1990 | Bateman et al. | 524/17 |
| 5,162,430 | 11/1992 | Rhee et al. | 525/54.1 |
| 5,264,214 | 11/1993 | Rhee et al. | 424/422 |
| 5,292,802 | 3/1994 | Rhee et al. | 525/54.1 |
| 5,304,595 | 4/1994 | Rhee et al. | 525/54.1 |
| 5,306,500 | 4/1994 | Rhee et al. | 424/422 |
| 5,376,375 | 12/1994 | Rhee et al. | 424/423 |

OTHER PUBLICATIONS

Steinbach, *Arzneim–Forsch/Drug Res.*, No. 42(1), pp. 85–89, 1992.
Okamura et al, *Chemical Abstracts*, vol. 68, p. 7692, Ref. #79646a, 1968.
Mohanaradbakrishnan et al, *Chemical Abstracts*, vol. 83, pp. 256–257, Ref. #73887t, 1975 (Arzneim–Forsh, 1975 25(5) 726–35).
Kato et al, *Chemical Abstracts*, vol. 113, p. 357, Ref. #120741R, 1990 (Biomaterials 1990, 11(3), (169–75).
Senatore et al, *Biotechnol. Bioeng.*, vol. 28(1), pp. 64–72, 1986.
Chvapil et al., "Medical and Surgical Applications of Collagen", *Connective Tissue Research*, vol. 4, pp. 1–61 (1973).
McPherson et al., "Collagen Fibrillogenesis In Vitro: A Characterization of Fibril Quality as a Function of Assembly Conditions", *Collagen Rel. Res.*, vol. 5, pp. 119–135 (1985).
Dr. Paul Brown et al., "Newer Data on the Inactivation of Scraple Virus or Crestzfedt–Jakob Disease Virus in Brain Tissue", *The J. of Infectious Diseases*, vol. 153, No. 6 (1986).
Wallace et al., "Multiple Denaturational Transitions in Fibrillar Collagen", *Journal of Biopolymers*, vol. 25, pp. 1875–1893, John Wiley & Sons (1986).
Dr. Steinbach, "Recommendations for Minimizing the Risk of Infection by Agents Causing Zoonoses and Other Animal Infections in Manufacture of Medicinal Products", *Arzneim–Forsch/Drug Res.*, No. 42 (1), pp. 85–89 (1992).
"Public Health Issues Related to Animal and Human Spongiform Encephalopathies: Memorandum from a WHO Meeting", *Bulletin of the World Health Organization*, No. 70 (2), pp. 183–190 (1992).

*Primary Examiner*—Elizabeth C. Weimar
*Assistant Examiner*—Abdel A. Mohamed
*Attorney, Agent, or Firm*—Shirley L. Church; Kathi Rafayko; Freddie K. Park

[57] ABSTRACT

In accordance with the present invention, stabilized dispersions of collagen fibers that have been treated in order to inactivate infectious agents and methods of stabilizing such collagen fibers are provided.

29 Claims, 9 Drawing Sheets

METHOD OF CONTROLLING STRUCTURE STABILITY OF COLLAGEN FIBERS PRODUCED FORM SOLUTIONS OR DISPERSIONS TREATED WITH SODIUM HYDROXIDE FOR INFECTIOUS AGENT DEACTIVATION

BACKGROUND OF THE INVENTION

1. Field of the Invention

The present invention relates to a method of controlling the structure stability of collagen fibers produced from solutions or suspensions of collagen which have been treated with a chemical reagent for the deactivation of infectious agents.

2. Description of the Background Art

There are public health issues pertaining to the use of animal and human tissues in medical devices which are implanted into human beings, to the use of such tissues in pharmaceuticals, and to a lesser degree, to use in cosmetics. Of particular concern are slow acting viruses present in such tissues, which slow viruses are particularly difficult to deactivate.

U.S. Pat. No. 4,511,653 to Play et al., issued Apr. 16, 1985, describes a process for the industrial preparation of human collagenous material from human placental tissue. This process includes subjecting the placental tissue to an alkaline treatment with a 0.5M solution of NaOH, a 0.5M solution of potassium hydroxide (KOH), or a saturated lime water solution at a temperature of less than or equal to 10° C., for purposes of inactivation of viruses.

In June of 1986, "Concise Communications", The Journal of Infectious Diseases, Vol. 153, No. 6, there is a description of the inactivation of slow acting viruses, such as scrapie virus and CJD virus present in 20% brain homogenates, using various concentrations of sodium hydroxide (NaOH) for one hour at room temperature.

In September of 1991, "Recommendations for Minimizing the Risk of Infection by Agents Causing Zoonoses and Other Animal Infections in Manufacture of Medicinal Products", Federal Journal of Official Publications (BAnz., Germany), No. 164, p 6120, there is the description of the treatment of medical materials with a solution of 1N (1M) NaOH for one hour at 20° C. for the purpose of inactivation of infectious agents. This treatment was recommended particularly for application to bovine spongiform encephalopathy (BSE) and materials of bovine origin.

In 1992, "Public Health Issues Related to Animal and Human Spongiform Encephalopathies": Memorandum from a WHO Meeting, Bulletin of the World Health Organization, 70(2): pp 183–190, a discussion is presented regarding BSE, a member of the group of transmissible spongiform encephalopathies (THE) whose prototype is scrapie. Treatment of medicinal products derived from bovine tissues with NaOH, preferably 1M, for 1 hour at 20° C. is recommended as a manufacturing process for removal or reduction of BSE infectivity.

Collagen Corporation, assignee of the present application, produces a variety of products having bovine collagen as a principal component. The source of Collagen's bovine collagen is a closed herd which is controlled to reduce the potential of contamination by a source of THE (or other infectious agent). It is questionable whether THE is present within the U.S.; however, due to the problem in foreign countries and the possibility of contamination of U.S. bovine supplies, it is desirable to have a method of treating animal tissues used in the preparation of implantable medical devices, medicinal products, and cosmetics. The sodium hydroxide (NaOH) treatment of such tissues has been demonstrated to be particularly effective in the reduction of infectious agents in general. With this in mind, the evaluation of a processes for NaOH treatment of collagen solutions and suspensions used to prepare collagen-based products was carried out.

Collagen may be obtained in commercially useful amounts from the connective tissues of a variety of domesticated animals, such as cattle and swine, for example. The native collagen is most conveniently obtained from tendons or skin and is freed from extraneous matter such as lipids, saccharides and non collagen protein, so as to leave the collagen protein free or substantially free of other connective tissue materials. Native collagen fibers are composed of regularly arranged subunit structures referred to as collagen molecules. Each collagen molecule is about 3000 Å long and 15 Å in diameter. This long rigid rod-like structure consists of three polypeptide chains wound together in a triple helical configuration. Typically two of the constituent chains are identical in composition and the third is different. A characteristic distribution of amino acid residues along the length of any given polypeptide strand, wherein repeating triplets contain glycine at every third position, favors the formation of a helical configuration. The individual collagen units form fibrils which associate to form fibers.

The nonhelical terminal portions of the native collagen molecule, the telopeptides, exhibit a preferred coil conformation extending from the amino and carboxy ends of the molecule. These telopeptides appear to serve a number of functions in the formation of the native collagen fiber. The telopeptides serve as the primary sites for crosslinking intramolecularly (between the three constituent polypeptide chains in the native collagen molecule) and intermolecularly (between two or more native collagen molecules). In addition, the telopeptides facilitate the arrangement of the individual collagen molecules in a pattern which provides for the regular structure of native fibrous collagen. However, the telopeptide portions of native (heterogenic) collagen are believed to be the major sites of its immunogenicity. Therefore, in order to minimize the immunogenicity of heterogenic collagen, it is desirable that the telopeptides be removed. This leaves the collagen fibers in a less stable, more fragile condition, and in need of protection when protection when exposed to processing conditions, which can disturb the arrangement (association) of collagen molecules within collagen fibers.

Typically collagen is obtained from bovine hides. The initial stage is to clean the hide physically so as to remove some of the noncollagen materials, such as hair, fat, carbohydrates, mucopolysaccharides and the like. See, for example, U.S. Pat. Nos. 2,934,446 and 3,121,049, as well as Chvapil et al., "Medical and Surgical Applications of Collagen", Connective Tissue Research 4 (1973).

To enhance the ease of purification and facilitate the enzymatic removal of the telopeptides, the collagenous material is subjected to various mechanical treatments, such as dissection, grinding, high speed shearing, milling and the like. Depending upon the particular treatment, the collagen may be wet or dry, frozen or cooled, with grinding and high speed shearing preferably being wet processes, and milling being a dry process.

Coarsely divided connective tissues are swollen in aqueous acidic solutions under nondenaturing conditions. Further dispersion is achieved through extensive wet grinding, to facilitate enzyme access to the native collagen. Preferably dilute acid solutions at low temperatures are employed to minimize denaturation. Suitable acids are acetic, malonic or lactic acids, or other lyotropic carboxylic acids having pK values from about 2 to about 5 at 25° C. Concentrations of acid in the dispersion medium range from about 0.01M to 1.0M, and temperatures may vary from about 4° C. to about 25° C. The dispersion which is obtained by treatment with acid is a viscous dispersion containing native collagen microaggregates and a small amount of native collagen in solution.

The viscous product is subjected to enzymatic treatment to remove the telopeptides and to produce soluble atelopeptide collagen. Various proteolytic enzymes may be employed which preferentially attack the telopeptides, while leaving the major portion of the molecule intact. Illustrative enzymes include pepsin, trypsin and pronase, for example. See U.S. Pat. Nos. 3,131,130 and 3,530,037.

The preferred enzyme is pepsin, which is used in combination with an acidic solution, generally at a pH of about 2 to 4. The concentration of the enzyme varies from about 0.001 to about 10 weight percent based on the weight of collagen present. The collagen concentration generally varies from 0.5 g/l. to about 10 g/l. Preferably, the acidity is provided by a carboxylic acid in a concentration of about 0.01M to about 1M. If necessary, the pH can be adjusted by the addition of a mineral acid, e.g. hydrochloric acid. The enzymatic treatment is generally carried out over temperatures ranging from about 0° C. to about 30° C. over a time period ranging between two days and two weeks, with progress monitored periodically until substantially complete solubilization of the collagen is achieved.

The resulting solution is treated to separate the soluble atelopeptide collagen from insoluble collagen, enzymes, residual amino acids, and the telopeptide units which have been separated from the collagen molecules. Primarily, the treatment involves separations, precipitations and dialysis against various solutions of different ionic strength. Moderate temperatures are employed, normally from about 4° C. to about 30° C., and salt solutions of various ionic strength or concentration are employed, generally from about 0.01M to 3.5M, depending upon the particular salt. Ionic strengths are usually about 0.01 to 3.5.

Conveniently, the solution is treated with an alkaline material, e.g., sodium hydroxide, to raise the pH of the solution to at least about seven, to inactivate the enzyme. After inactivating the enzyme, non-solubilized contaminants which have been precipitated during the inactivation treatment are filtered off to yield a filtrate which contains collagen in solution.

The collagen in solution is passed through a bed of celite and subsequently processed via ultrafiltration to provide a purified, clear solution containing about 3 mg/ml of atelopeptide collagen. This concentrated solution of collagen is relatively free of higher aggregates, and is referred to as concentrated submicron filtrate (CSF).

From a virus deactivation/inactivation point of view, it is preferable to treat a solution of collagen with sodium hydroxide for virus inactivation prior to the formation of the fibrous micropolymers, since the collagen molecules and any beginning fibrils contained in the solution are dissociated to permit maximum availability of any infectious agents which may reside in or be trapped within fiber structures. The collagen triple helix is too tightly wound (1.5 nm diameter) for a virus to reside within the collagen molecule.

Therefore, such virus would be present either in the solution or absorbed onto the surface of a collagen molecule. In the soluble environment, where collagen fibers are dissociated into collagen molecules, there is no mass transfer barrier, which requires the sodium hydroxide to diffuse through solids (assembled fibers) to reach the infectious agents on the surface of collagen molecules.

During the evaluation of NaOH treatment of collagen solutions and suspensions, it was discovered that the structure of the collagen fibers formed was affected by the 1.5 NaOH treatment. The fibrillar collagen produced from solutions and suspensions of NaOH treated collagen exhibited significantly different polymeric characteristics.

To be able to use the NaOH treatment of collagen solutions for deactivation of infectious agents, it was necessary to find a method to compensate for the effects of the treatment, enabling production of the desired fibrillar collagen product. The fibrous collagen product had to be biocompatible and sufficiently stable that it was relatively insensitive to contact with chemical additives and to processing necessary to achieve final product formulation.

SUMMARY OF THE INVENTION

In accordance with the present invention, it has been discovered that the stability of collagen fibers is altered upon treatment of a solution or dispersion of the collagen fibers with a chemical reagent for the inactivation of infectious agents. This fiber destabilization makes it difficult to formulate the collagen fibers to final product when the formulation contains an ingredient which alters the destabilized collagen fibers.

Collagen fiber stability is controlled using either a physical means or a chemical means. The physical means is used to protect the stability of the assembled fibers, without providing for covalent bonding between fibrils. The chemical means is used to provide covalent bonding between fibrils, whereby the fibers are stabilized.

A stabilized collagen fiber is achieved by the presence of a physical fiber-stabilizing means (agent) comprising a water soluble or water miscible polymeric material of the kind which is capable, at sufficient concentration, of causing collagen fibers to precipitate from solution. These water soluble or water miscible polymeric materials are typically polyvinyl alcohol, polyethylene oxide, polyvinylpyrrolidone, polyacrylamide, polyethylene glycol or derivatives thereof, polypropylene glycol or derivatives thereof, polyvinyl methylether, maleic anhydride copolymers, hydroxyethyl starches, methyl cellulose, hydroxymethyl cellulose, hydroxyethyl cellulose, hydroxypropyl cellulose, agarose, dextrins, dextrans, pectins and alginates, for example. Preferably the water soluble or water miscible polymeric material is biocompatible, such as a polyethylene glycol (PEG) or derivatives thereof.

A stabilized collagen fiber is also prepared by using a chemical agent which crosslinks the fiber, stabilizing the fiber. Preferably the crosslinking agent is also biocompatible, such as a glutaraldehyde, hexamethyl diisocyanate, dimethyl suberimidate, carbodiimide, or an activated PEG.

One method of stabilizing the collagen fiber produced from a solution or a dispersion of collagen treated with a chemical reagent for the inactivation of infectious agents is to stabilize the collagen fiber subsequent to the treatment by using at least one of the physical or chemical fiber-stabilizing agents described above.

A second, less preferable, method of stabilizing the collagen fiber is to use a physical fiber-stabilizing agent prior to or simultaneously with treatment using the agent for deactivation of infectious agents.

Preferably, sodium hydroxide is the chemical reagent used to inactivate infectious agents in the method of the present invention.

BRIEF DESCRIPTION OF THE DRAWINGS

FIG. 2A shows DSC Curve 200 for a collagen dispersion prepared from a solution of collagen without sodium hydroxide treatment of the solution, where the collagen dispersion was formulated to a final product containing 35 mg/ml collagen at a pH of 7.0 to 7.4, using a water base solution containing 3 mg/ml lidocaine, 0.13M sodium chloride, and 0.02M disodium phosphate. FIG. 2B shows DSC Curve 220 for a final product containing 35 mg/ml collagen at a pH of 7.0 to 7.4, prepared from a collagen solution treated with sodium hydroxide, and formulated to final product using a water base solution containing 0.13M sodium chloride and 0.02M disodium phosphate. FIG. 2C shows DSC Curve 230 for a final product containing 35 mg/ml collagen at a pH of 7.0 to 7.4 prepared from a collagen solution treated with sodium hydroxide, and formulated to final product using a water base solution containing 3 mg/ml lidocaine, 0.13M sodium chloride, and 0.02M disodium phosphate.

FIG. 5B, Curve 511 shows the gel frequency response data for a dispersion of collagen fibers prepared from a sodium hydroxide-treated solution; Curve 513 shows the gel frequency response data for the same dispersion when 10 mg/ml of PEG physical fiber-stabilizing agent is added to the 35 mg/ml collagen dispersion during formulation to final product. FIG. 5C, Curve 520 shows gel frequency response data for another dispersion containing 35 mg/ml of collagen fibers, prepared from a sodium hydroxide-treated solution; Curve 522 shows the gel frequency response data for the same dispersion when 2.5 mg/ml of PEG physical fiber-stabilizing agent is added during formulation to final product.

DETAILED DESCRIPTION OF THE PREFERRED EMBODIMENTS

Figure 1:
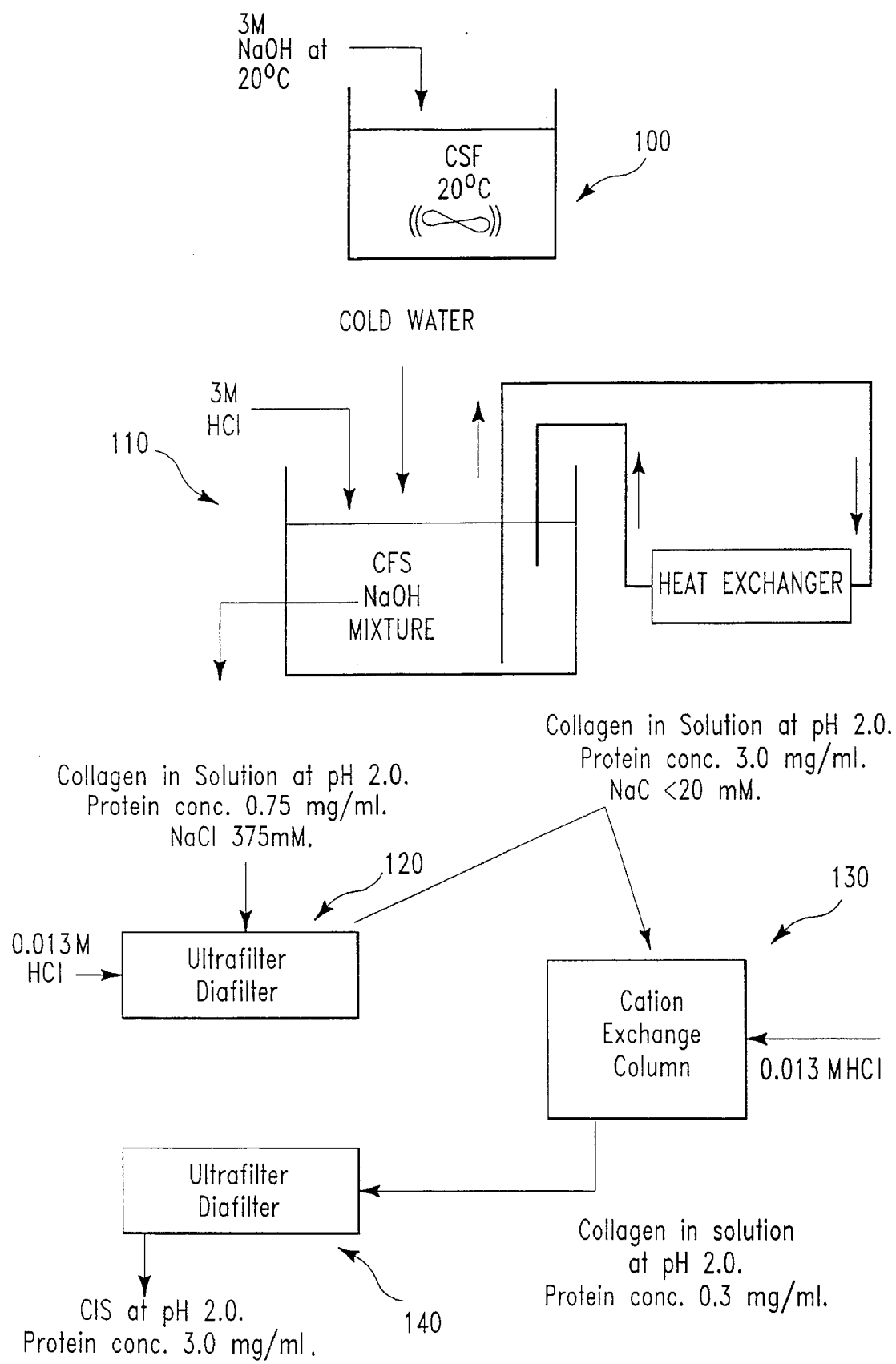
FIG. 1 shows a process flow diagram for a typical treatment of collagen in a solution or suspension with a chemical reagent for deactivation/inactivation of infectious agents. In this instance, the collagen is in the form of a solution, concentrated submicron filtrate (CSF), at the beginning of treatment, and the chemical reagent is sodium hydroxide.

In accordance with the present invention, collagen solutions or suspensions are treated with sodium hydroxide (NaOH) to deactivate infectious agents. The stabilization of collagen fibers formed from a treated solution of collagen molecules; from a treated suspension of collagen fibrils and fibers; or from a mixture containing both collagen molecules and collagen fibrils and fibers, is controlled using either at least one physical fiber-stabilizing agent, at least one chemical fiber-stabilizing means, or a combination thereof. The physical fiber-stabilization means are used to control fiber stability without providing for covalent bonding between fibrils within assembled (associated) fibers. The chemical fiber-stabilizing means are used to provide covalent bonding between fibrils, whereby the fibers formed from the fibrils are stabilized.

EXAMPLES

Example 1

Treatment of Collagen Solution with Sodium Hydroxide

Concentrated Submicron Filtrate (CSF) collagen solution, prepared in the manner previously described, was treated with sodium hydroxide to develop an acceptable process for scaling up to a manufacturing process.

A. 600 ml of soluble collagen as CSF (3.0 mg/ml protein, pH 2.0) was brought up to 1M sodium hydroxide (NaOH) by the addition to 300 ml of 3M NaOH (in a volumetric ratio of 2:1 of CSF: NaOH) over a 15 minute time period. The addition of sodium hydroxide was done using a peristaltic pump and the mixture was stirred throughout the addition. The mixture was then incubated at 20° C. for 63±3 minutes (not a critical time period). The mixture was then cooled by recirculating it for 5 minutes through 5 ft. of 316 L stainless steel tubing (OD=0.125 in., ID=0.097 in.) immersed in a cold water bath. Simultaneously, during the recirculation, 600 ml of chilled water (~6° C.) was pumped into the mixture over a 5 minute period. The addition of chilled water helped cool the mixture and also provided a 40% reduction in NaOH concentration within 5 minutes. The sodium hydroxide in the mixture was then neutralized by the addition of approximately 300 ml of 3M HCl over 15 minutes using a peristaltic pump. During the neutralization, the mixture was recirculated through the stainless steel tubing immersed in the cold water bath to remove the heat generated by the exothermic acid/base reaction. The temperature of the mixture during the addition of the 3M HCl was maintained below 17° C. The pH of the neutralized mixture was then adjusted to 2.0 using 1M HCl; 600 ml of water was also added to reduce the salt concentration in the mixture. The diluted mixture (~2400 ml) was then concentrated to approximately 600 ml (2.5–3.0 mg/ml protein, essentially collagen) using the Filtron® Ultrasette Omega series Polyethersulfone membrane (MWCO 100 kD), available from Filtron Corp., Northborough, Mass. The concentrated mixture was then diafiltered at constant volume with 1800 ml of 0.0013M HCl using the same membrane described above. The diafiltration reduced the residual salt concentration to less than 20 mM. The resulting material was ultafiltered to provide a CSF as nearly equivalent as possible to the CSF prior to treatment with NaOH.

B. In addition to the above three processes, a smaller scale laboratory process, about 200 ml in volume, was employed to independently evaluate the effects of the sodium hydroxide treatment on the stability of fibers formed from treated solutions or suspensions.

Due to the reduced volumetric scale of this process, the addition of sodium hydroxide was done over a 10 minute time period. After incubation at about 20° C. for about 60–65 minutes, cold water (≈4° C.) was added to quickly quench any sodium hydroxide reaction. The volume of cold water added was about 8 times the CSF volume. The diluted mixture was neutralized with cold hydrochloric acid (≈4° C.) over a 10 minute period. The mixture, having a pH of about 2.0, was concentrated to approximately 3.0 mg/ml of collagen and then diafiltered at constant volume against at least 4.5 volumes of 0.013M hydrochloric acid. The addition of a large volume of cold water prior to neutralization with hydrochloric acid reduced the sodium hydroxide concentration in the mixture to approximately 0.15M, and the temperature to about 6° C. As a result, the process temperature after the sodium hydroxide treatment was maintained below about 6° C. and the effects observed due to sodium hydroxide treatment were attributed to the exposure to 1M sodium hydroxide at 20° C. for about 60–65 minutes.

While the majority of laboratory trials were done using the processes described in Example 1A and illustrated in FIG. 1, a few of the experiments were carried out using process 1B. The Example 1A process was used in all examples from which collagen fiber stability was determined, unless otherwise specified.

With reference to FIG. 1, in step 100, clarified submicron filtrate (CSF) bovine collagen, comprising atelopeptide collagen at a concentration of about 3.0 mg/ml in protein, having a pH of about 1.9–2.2 was treated with 3M sodium hydroxide (NaOH), which was mixed into the CSF, to bring the CSF solution to a concentration of 1M NaOH. The addition of the NaOH to the CSF solution was carded out at atmospheric pressure (exposed to air) and at a temperature of about 20° C. The 3M NaOH was added to the CSF over a time period of about 10 minutes, followed by incubation at about 20 ° C. for a period of about 60–65 minutes. Contact of the CSF with the NaOH produced a solution which was 1M in NaOH, with a resulting pH of slightly less than about 14.

U.S. Patent Application, Ser. No. 08/201,860, filed Feb. 17, 1994, and assigned to the assignee of the present application, describes the use of pH manipulation and/or addition of a salt to control fiber size during precipitation of fibrous collagen from solution. In particular, the pH of the starting collagen suspension in an aqueous medium was adjusted to 5 or less to permit fiber disassembly (permit the collagen to go into solution); subsequently the pH of the medium was adjusted over a range of 6 to 9 to produce various fiber size populations. At a pH above about 10, the fibers begin to disassemble and return to solution. An increase in pH, up to about 10, resulted in an increase in fiber size, i.e., produced a fiber population having an increased number of larger fibers (indicated by light scattering techniques). Further, addition of a salt (NaCl) to the collagen solution produced a fiber population which was shown by differential scanning calorimetry to have multiple transition temperatures with two major endotherms, indicating the disruption of the collagen fiber structure and partial disassembly of the collagen fibers due to the presence of the salt.

In the present instance, as shown in FIG. 1, step 110, after the sodium hydroxide treatment, cold water (≈8° C.) was added over a time period of about 5 minutes. The volume of water added was about equivalent to the original CSF volume. The diluted mixture was neutralized using 3M hydrochloric acid (HCl) added to the CSF/NaOH mixture to adjust the OH of the mixture to about 2.0, enabling the formation of a collagen solution at this pH. The HCl was added over a 15 minute time period, and the process mixture was circulated through a heat exchanger to remove the heat generated by the exothermic acid/base reaction, maintaining a temperature for the mixture of around 16° C. The pH 2 solution produced contained about 0.75 mg/ml of collagen molecules and a NaCl concentration of about 375 mM.

The mixture produced in step 110 was concentrated in step 120 to 3.0 mg/ml of collagen by Ultrafiltration/Diafiltration, standard membrane filtering techniques known in the industry. The diafiltration was done at constant volume with at least 3 volumes of 0.013M hydrochloric acid, to ensure that the filtered solution would remain at a pH of about 2.0. The filtered solution exhibited a residual salt concentration of less than 20 mM NaCl.

The collagen solution produced in step 120 was further purified through a batch cation exchange column (a 2,400 ml batch column), as shown in FIG. 1, step 130, and eluted in a two stage elution at about 1,660 ml/stage in combination with HCl at an elution pH of 2.0, to produce a collagen solution containing about 0.3 mg/ml protein.

The eluate was then concentrated in step 140 to about 2.5 to 3.0 mg/ml protein by Ultrafiltering and then Diafitering in combination with at least 2,5 volumes of 0.013M HCl (pH 2.0), using the Filtron® membrane previously described.

This diafiltration produced a ten-fold reduction in acetate in the column eluates, decreasing residual acetate concentration to less than 1 mM. The resulting collagen in solution was expected to be equivalent to that produced in a process where the CSF was not treated with sodium hydroxide. This concentrated, purified collagen solution, having been treated for deactivation of infectious agents, was then ready for final processing into desired end products.

Example 2

Preparation of a Non-crosslinked Fibrous Collagen Suspension

The concentrated, purified collagen solution processed as described in Example 1A and illustrated in FIG. 1, is typically used to prepare an injectable water based dispersion of fibrous, non-crosslinked collagen of the kind sold by Collagen Corporation under the trademark Zyderm®. A solution, prepared in the manner described in Example 1A, at 3.0 mg/ml protein was precipitated at about 17° C. by the addition of 0.2M Disodium Phosphate buffer adjusted to a pH of 11.2 using sodium hydroxide. The volumetric ratio of collagen solution to buffer was 9:1. The precipitate produced contained a fibrous collagen concentration of approximately 2.7 mg/ml. The precipitate was concentrated by centrifugation to a protein content in excess of 35 mg/ml. Formulation to final product was made by diluting the centrifugate with a water-based solution comprising 0.02M disodium phosphate, 3 mg/ml lidocaine (localized anesthetic), and 1.3M sodium chloride (NaCl), at a pH of 6.3. The resulting product comprised an aqueous dispersion containing about 35 mg/ml of fibrous collagen, 3 mg/ml of lidocaine, 0.02M disodium phosphate, and 0.13M sodium chloride, at a pH of 7.0–7.4.

The "Zyderm", non-crosslinked, fibrous collagen product produced was compared with a Zyderm® control product prepared without an NaOH treatment for inactivation of infectious agents. The control was prepared from CSF purified and concentrated using the cation exchange column, with subsequent ultrafiltration and diafiltration as described above, with reference to FIG. 1 steps 130 and 140. It was discovered that the fibrous collagen product prepared from an NaOH—treated collagen solution marginally passed or failed Zyderm® product specifications for Differential Scanning Calorimetry and Opacity. Differential Scanning Calorimetry and Opacity are used as indicators of collagen fiber size population distribution. See, for example, Wallace et al., Journal of Biopolymers, Vol. 25, p. 1875 (1986) and McPherson et al., Collagen Related Research, Vol. 5, pp. 119–135 (1985), respectively.

Figure 2A:
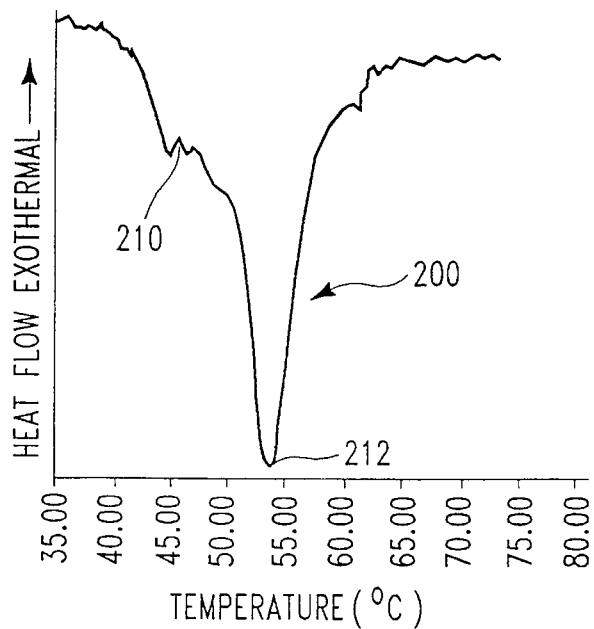
FIGS. 2A, 2B, and 2C show differential scanning calorimetry (DSC) thermograms for collagen dispersions prepared using the methods described in Example 1C.

FIG. 2A shows the differential scanning calorimetry (DSC) Curve 200 for collagen fibers prepared from a collagen solution without sodium hydroxide treatment, formulated to a water based dispersion containing about 35 mg/ml of collagen fibers, 3 mg/ml of lidocaine (localized anesthetic), 130 mM of sodium chloride, and 0.02M disodium phosphate, at a pH of about 7.0–7.4. The DSC curve for the collagen dispersion exhibits two peaks, a minor peak 210 at about 46° C., and major peak 212 at about 54° C. This indicates the formation of two fiber size populations, with the minor population at 210 representing some portion of the collagen fibers having a smaller average fiber size (which have apparently been produced as a result principally of the addition of the lidocaine and secondarily of the salt to the suspension of collagen fibers) and a major population at 212, representing a larger average fiber size (of the kind typically observed for collagen fibers produced from a solution of collagen not treated with sodium hydroxide).

Figure 2B:
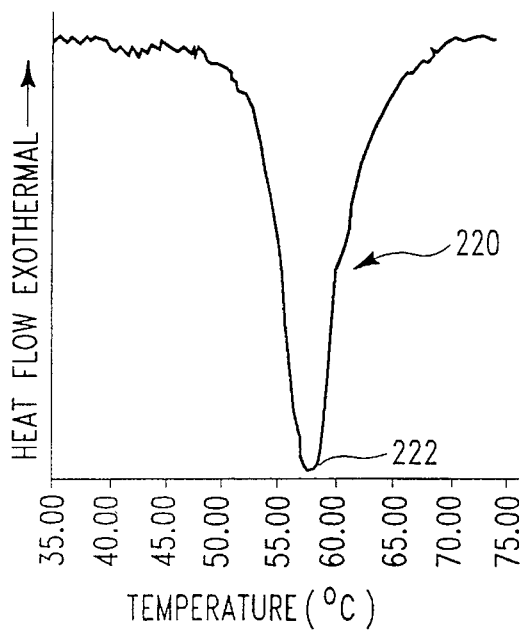

FIG. 2B shows DSC Curve 220 for a collagen dispersion prepared with sodium hydroxide treatment, but formulated with 0.13M sodium chloride and 0.02M sodium phosphate, only (without lidocaine), at a pH of 7.0–7.4. Only one peak 222 is evident, at about 57° C. This represents the formation of a single fiber size population with an average fiber size approximately equal to the average fiber size observed for the larger collagen fibers shown in FIG. 2A.

Figure 2C:
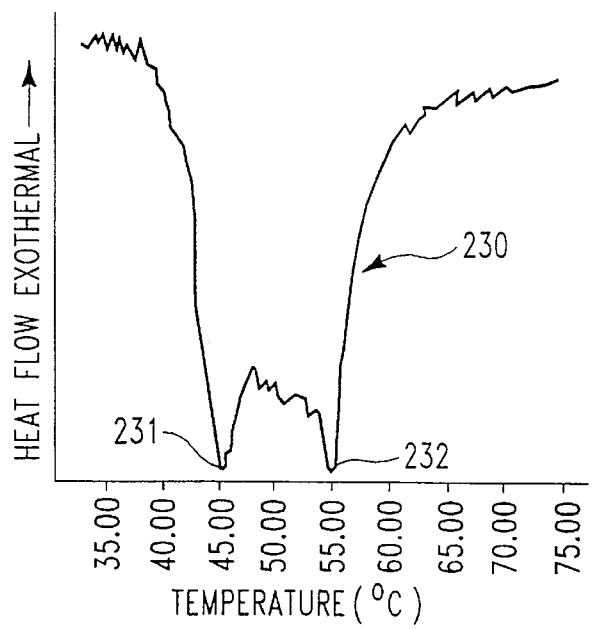

FIG. 2C shows DSC Curve 230 for a collagen dispersion prepared with sodium hydroxide treatment, which was formulated to a 35 mg/ml fibrillar collagen concentration, with 3 mg/ml of lidocaine and 130 mM of sodium chloride, at a pH of 7.0–7.4. Again, when the lidocaine and sodium chloride are present in the diluting medium, two peaks are evident, a first peak 231 at about 45° C., representing the fiber population having a smaller average fiber size, and a second peak 232 at about 55° C., representing the larger average fibers size. The peaks 231 and 232 shown in Curve 230 are approximately equal in size, indicating approximately equal quantities of collagen in each fiber size population.

A comparison of DSC curves 200 and 230 indicates that the sodium hydroxide treatment of the collagen in solution prior to its processing to form fibers altered the stability of the collagen fibers produced. Curve 200 shows a collagen dispersion prepared from non-sodium hydroxide-treated collagen solution, which exhibits a first, larger average fiber size population 212, and a second, smaller average fiber size population 210 (after formulation to final product in the presence of lidocaine). The collagen dispersion prepared from a sodium hydroxide-treated collagen solution, shown in Curve 230, exhibits a grossly increased amount of the second, smaller average fiber size population 231 after the same formulation to final product.

Although not shown in FIG. 2, the DSC curve for a collagen dispersion prepared without sodium hydroxide treatment, and without the addition of lidocaine and sodium chloride upon dilution, also shows a single peak, basically the same at that of curve 220, for the collagen fiber population distribution.

A comparison of FIG. 2B, Curve 220, with FIG. 2C, Curve 230, confirms the fact that it is the addition of the lidocaine (localized anesthetic) which disrupts the stability of the collagen fibers, leading to the formation of a second fiber population having a smaller average fiber size.

The increased instability of the collagen fibers produced using sodium hydroxide treatment for deactivation of infectious agents is further supported by light transmission data indicating the same alteration of average fiber size populations. For example, the opacity at 410 nm, 0.1 path length, measured using a 0.1 cc quartz cuvette on a Beckman Model DU 650 spectrophotometer, for the collagen dispersion shown in FIG. 2A is 1.85 absorbance; the opacity measurement for the collagen dispersion shown in FIG. 2B is 2.1; and the opacity measurement for the collagen dispersion shown in FIG. 2C is 0.8. For a given concentration of collagen fibers in the dispersion measured, the larger the average fiber size, the higher the opacity measurement. Thus, opacity for the single, large average fiber size population of FIG. 2B is the highest; followed by the opacity for the collagen fibers of FIG. 2A, which have the dual fiber size population with the smallest quantity of collagen fibers having the smaller average fiber size; followed by the opacity for the collagen fibers of FIG. 2C, which have the dual fiber size population with the largest quantity of collagen fibers having the smaller average fiber size.

Example 3

Modification of the Process for Preparation of a Non-Crosslinked Fibrous Collagen Suspension: Physical Process The collagen fibers produced from sodium hydroxide treated solutions (produced by the method described in Example 1A, for example) can be stabilized to prevent alteration upon exposure to chemicals and/or processes necessary to formulate to final product. The physical process for such stabilization involves addition of an agent which protects the fibers from dissociation upon contact with chemicals or exposure to processing conditions.

In the present instance, it was desired to provide a fibrous collagen which would be stable in the presence of chemical additives and potentially adverse processing conditions used in preparing a final formulation containing the fibrous collagen. It was apparent that formulation to final product by the addition of a diluent containing salts and lidocaine (during the preparation of Zyderm, for example) was causing the collagen fibers to disassociate. It was unknown whether the collagen fibers would have to be stabilized prior to precipitation, or whether precipitated fibers could be stabilized subsequent to precipitation, simultaneously with formulation to final product.

The most preferred stabilizing agents are those which are biocompatible, nonimmunogenic and otherwise suitable to remain in the finished formulation, because these agents do not have to be removed from the finished formulation. With this in mind, the stabilizing agent used to demonstrate the concept of fiber stabilization was a biocompatible molecule, polyethylene glycol (PEG).

PEG is a biocompatible molecule which has been widely used in pharmaceutical industry formulations. There are a wide array of commercially available polyethylene glycols and derivatives thereof. The more commonly used polyethylene glycols range in weight average molecular weight from about 200 to about 20,000, with 200 to about 8,000 being preferred, and 300 to 6,000 being most preferred. Derivatives of polyethylene were not evaluated in the preferred embodiments, but would be expected to work as stabilizing agents provided they have surface functional characteristics which are substantially the same as PEG. Other biocompatible, water soluble or water miscible polymers which tend to cause precipitation of collagen fibers from collagen solutions (such as those described in U.S. Pat. No. 4,980,403), are expected to work as fiber-stabilizing additives.

U.S. Pat. No. 4,980,403 describes the use of water-soluble or water-miscible polymers to cause precipitation of collagen fibers from collagen solutions. Among the polymers listed as useful in achieving precipitation are polyvinyl alcohol, polyethylene oxide, polyvinylpyrrolidone, polyacrylamide, polyethylene glycol, polypropylene glycol, polyvinyl methyl ether, and maleic anhydride copolymers. Other natural polymeric materials listed include hydroxyethyl starches, methyl cellulose, hydroxymethyl cellulose, hydroxyethyl cellulose, hydroxypropyl cellulose, agarose, dextrins, dextrans, pectins and alginates. The use of such water-soluble or water-miscible polymers to aid in precipitation of collagen fibers from collagen solutions is said to be preferable to the addition of a neutral salt or a decrease in pH in the presence of a neutral salt, which is said to cause denaturation and disruption of the natural rod-like character of collagen.

In the present instance it was discovered that the addition of a physical fiber-stabilizing agent to the collagen solution during treatment of the solution with sodium hydroxide did not fully provide the degree of fiber stabilization desired. An improvement in fiber stability upon formulation to final product was observed for collagen dispersions prepared with a physical stabilizing agent present during sodium hydroxide treatment, however. Optimization of the amount of physical fiber-stabilizing agent present and of process conditions should even further improve this method of fiber stabilization.

Figure 3:
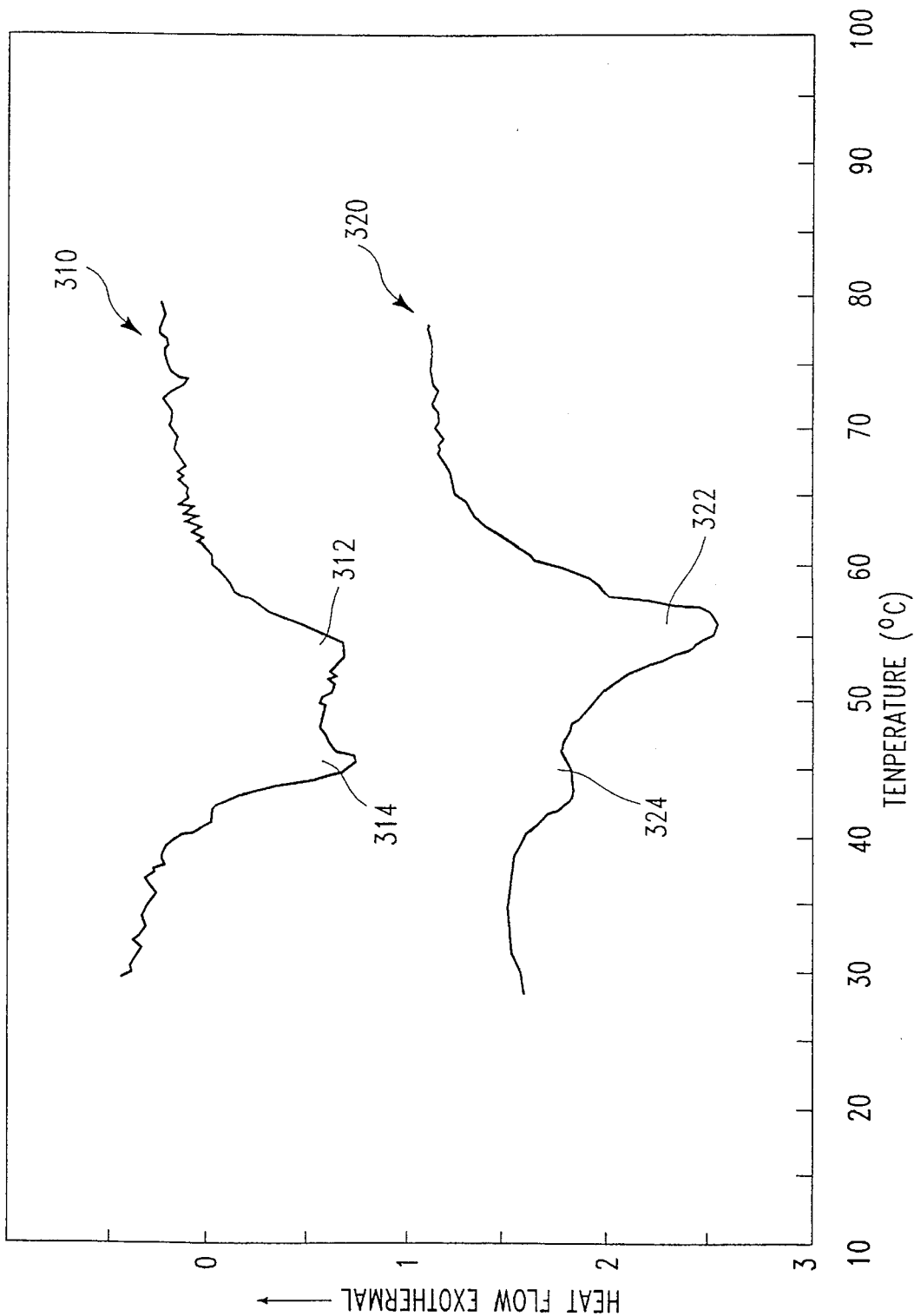
FIG. 3 shows DSC Curves 310 and 320 for collagen dispersions produced from a collagen solution treated with sodium hydroxide in the manner described in Example 1A. Curve 310 illustrates the control dispersion of collagen, where no PEG was added for purposes of fiber stabilization. Curve 320 illustrates the collagen dispersion formulated to final product where 50 g/l of PEG (8 kD) was present during the sodium hydroxide treatment, with no PEG added at time of formulation to final product.

The effect of the presence of a physical fiber-stabilizing agent during sodium hydroxide treatment is illustrated in FIG. 3. FIG. 3 shows DSC curves for collagen dispersions formulated to final product containing lidocaine and salts, where the collagen solution was treated with sodium hydroxide in the manner described in Example 1A. Curve 310 shows a collagen dispersion prepared from a collagen solution treated with sodium hydroxide with no physical fiber-stabilizing agent present. Curve 320 shows a collagen dispersion prepared from a collagen solution treated with sodium hydroxide in the presence of 50 g/l of PEG (8 kD), with no additional PEG added upon formulation to final product. The CSF—NaOH mixture was purified and concentrated as previously described, and subsequently formulated to final product containing 3 mg/ml of lidocaine, 0.13M sodium chloride, and 0.02M sodium phosphate, to a pH of 7.0–7.4 to provide the collagen dispersion tested, in each instance. It is readily apparent from DSC curves 310 and 320, that the presence of PEG during the sodium hydroxide treatment reduced the amount of the fiber population having a smaller average fiber size, as that population decreased from the amount shown as 314, in Curve 310 to the amount shown as 324, in Curve 320. However, the amount of smaller average fiber size population shown at 324, in Curve 320 substantially exceeds the amount present in collagen dispersions prepared from non-sodium hydroxide-treated solutions.

Since it is desired to maintain the collagen molecules in solution during treatment of the solution with sodium hydroxide (to provide maximum exposure of the infectious agents to sodium hydroxide, as previously described), the amount of PEG which should be added to the collagen solution is less than the amount which will cause a substantial amount of collagen fiber formation. It was determined that at a sodium hydroxide concentration of 1M (pH $\approx$14) and a collagen concentration of about 2.0 mg/ml, the following amounts of PEG can be added to the collagen solution, depending on the molecular weight of the PEG, without causing substantial fiber formation: for a PEG of 3.3 kD, 0–130 g/l of collagen containing solution; for a PEG of 8 kD, 9–75 g/l of collagen-containing solution; for a PEG of 20 kD, 0–45 g/l of collagen-containing solution.

It was subsequently discovered, unexpectedly, that addition of a fiber-stabilizing agent during formulation to final product alone stabilized the collagen fibers, enabling the preparation of collagen dispersions equivalent to those produced from collagen solutions which had not been treated with sodium hydroxide. This was unexpected, since one skilled in the art would believe that stabilization of the fibers during the sodium hydroxide treatment step should provide a fiber which remains stable during formulation to final product, and that such stabilization would indicate that addition of the stabilizing agent to the buffers used in formulation to final product would likely be less successful.

Figure 4:
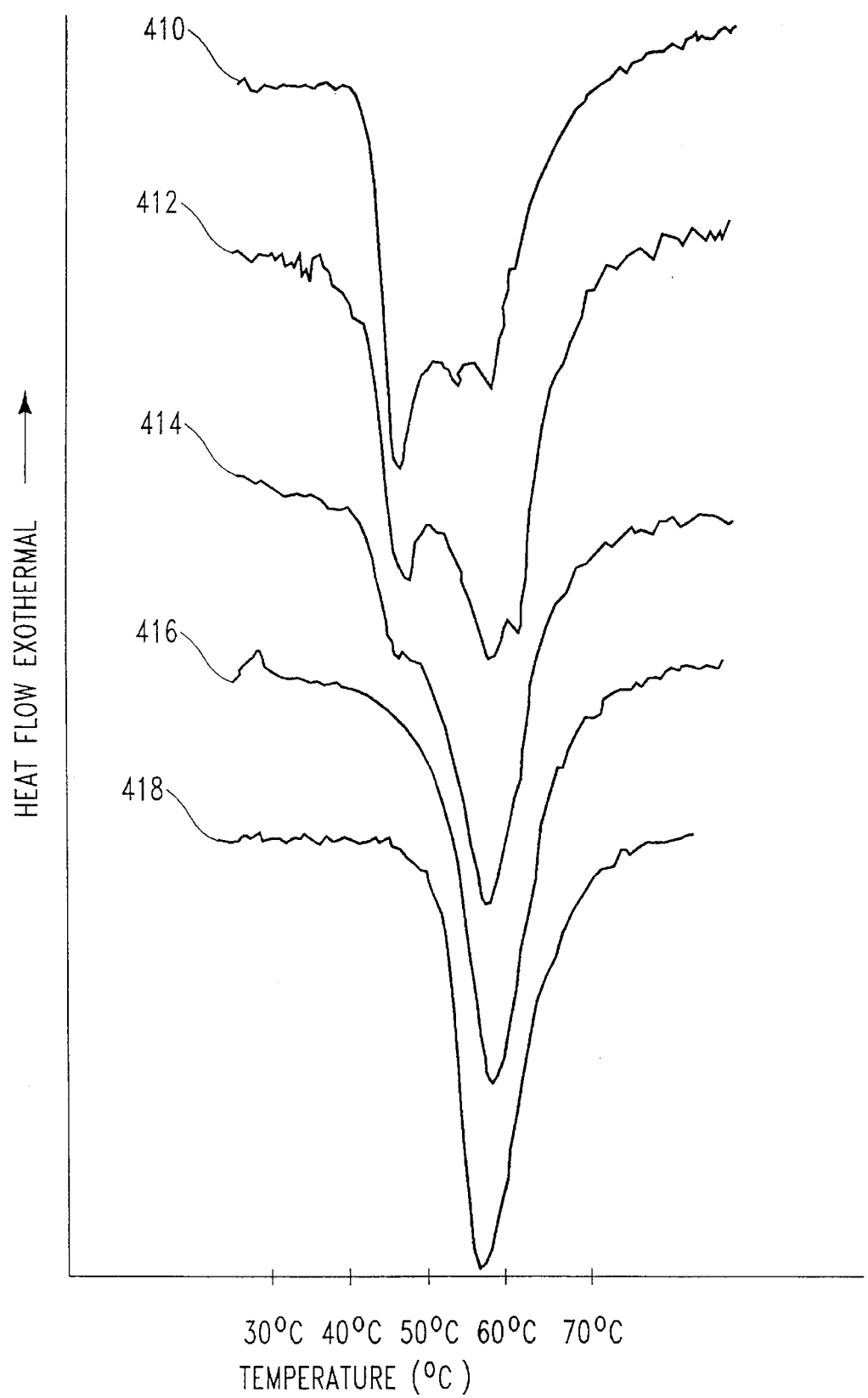
FIG. 4 shows a series of DSC curves for collagen dispersions produced from a collagen solution treated with sodium hydroxide in the manner described in Example 1B, where various amounts of PEG were added only during formulation to final product.

FIG. 4 shows the DSC curves for collagen dispersions produced from a collagen solution treated in the manner described in Example 1B; purified and concentrated as previously described; and, formulated to final product with a solution containing lidocaine, salts and various amounts of PEG. The amount of lidocaine and salts were those adequate to produce a final product containing 35 mg/ml of protein, 3 mg/ml of lidocaine, 0.13M sodium chloride and 0.02M sodium phosphate at a combined pH of 7.0–7.4. The amount of PEG (3.4 kD) used ranged from no PEG to about 10 mg/ml PEG. FIG. 4, curve 410, shows the effect of the absence of PEG during formulation to final product; Curve 412 shows the effect of 1 mg/ml of PEG; curve 414 shows the effect of the presence of 2.5 mg/ml of PEG; Curve 416 shows the effect of the presence of 5.0 mg/ml of PEG; and Curve 418 shows the effect of the presence of 10 mg/ml of PEG. It is readily apparent that the addition of PEG during formulation to final product stabilizes the collagen fibers and prevents disassembly of a first fiber population of larger sized fibers into a second fiber population of smaller fiber size.

Figure 5A:
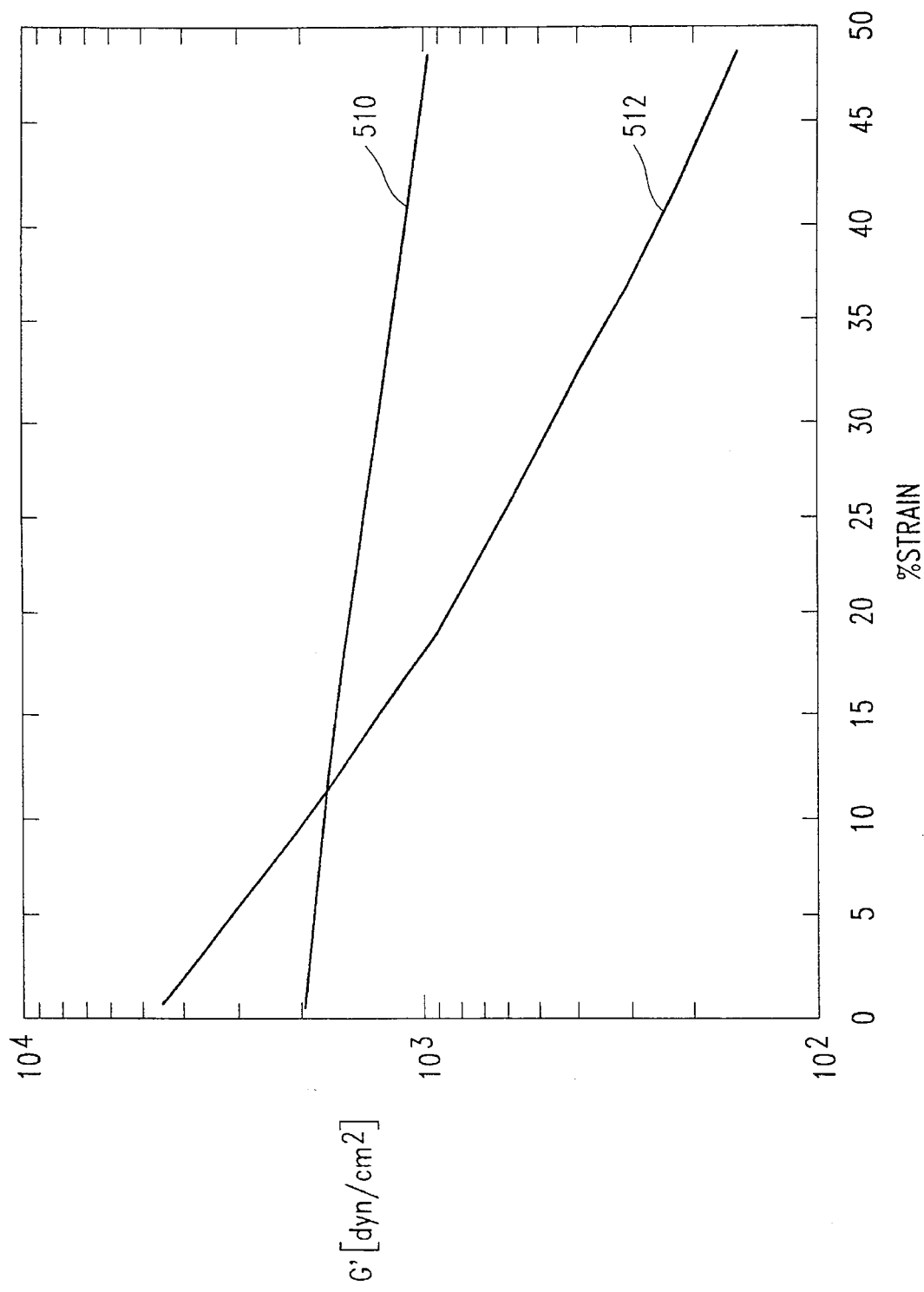
FIG. 5A shows the rheological characteristics, measured at 20° C. and 1 rad/sec, for a dispersion of collagen fibers containing 35 mg/ml of collagen, produced from a sodium hydroxide treated solution and formulated to final product in the presence of lidocaine (localized anesthetic) and a salt. Curves 510 and 512 show storage modulus vs. % strain, for collagen fibers formulated to final product without a physical fiber-stabilizing agent, and in the presence of a physical fiber-stabilizing agent, respectively.
Figure 5B:
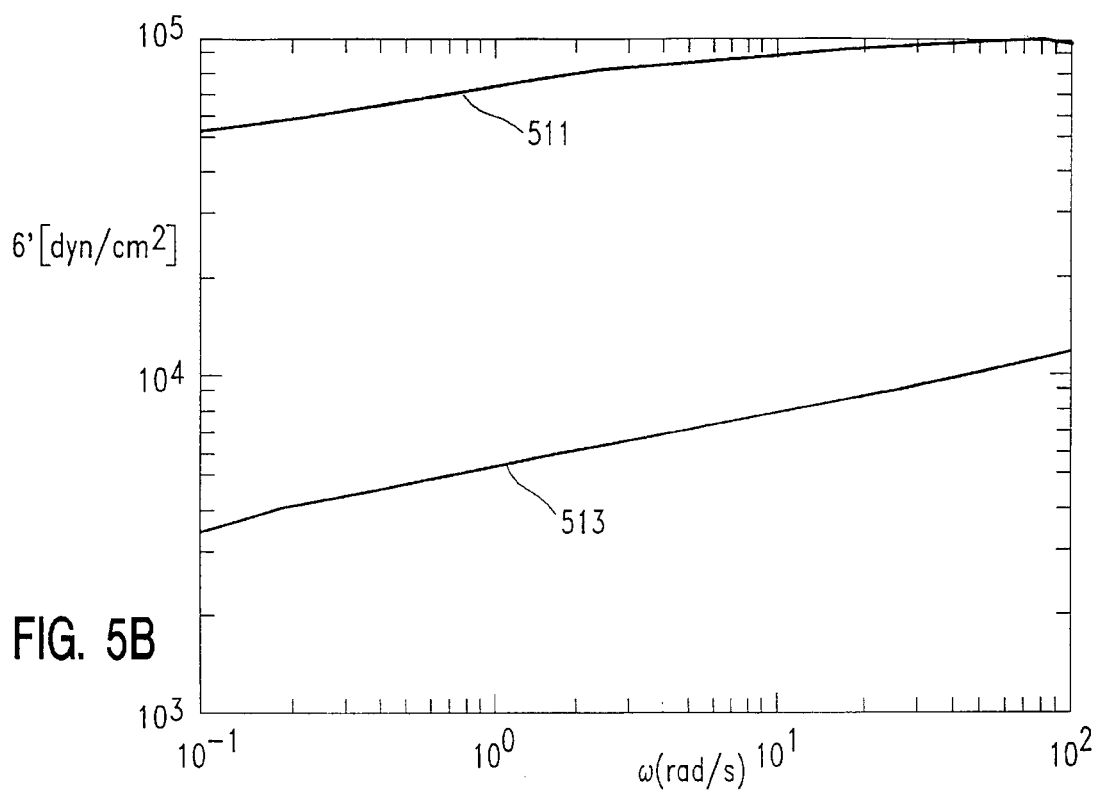
FIGS. 5B and 5C show gel elasticity data measured at 37° C. for dispersions containing 35 mg/ml of collagen.
Figure 5C:
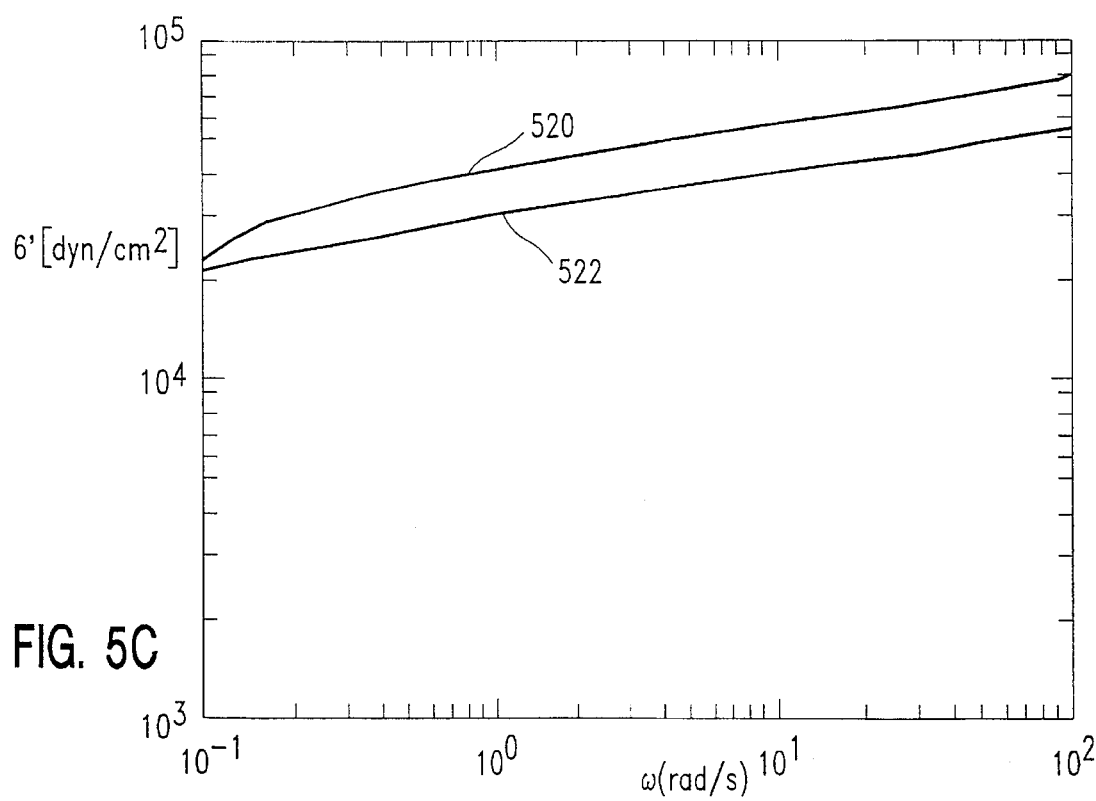

However, the presence of PEG in the final product formulation affected the rheological properties of the material. At high PEG concentrations (10 mg/ml), the material showed a strong strain-thinning behavior. FIG. 5 shows the plot of modulus v. % stress for product formulations. The measurements were carried out using a Model 8400 Fluid Spectrometer, parallel plate configuration of 25 mm diameter plates at 20° C. and 1 rad/sec, available from Rheometrics, Inc., Piscataway, N.J. FIG. 5A, Curves 510 and 512, show storage modulus versus % strain, where Curve 510 represents the formula without PEG and Curve 512 represents the formulation containing 3.3 kD PEG at a concentration of 10 mg/ml. The decrease in modulus with increasing strain when PEG is present translates into differences in the extrusion properties of the material through an injection needle, for example. In addition, at 37° C. the collagen dispersion formulated to final product with PEG present forms a weaker gel than the dispersion formulated to final product without PEG. FIG. 5B shows Curve 511, illustrating the gel elasticity data for a dispersion of collagen fibers formulated to final product. FIG. 5C, Curve 520 shows the gel elasticity for a second collagen dispersion formulated to final product, where the preceding collagen solution was sodium hydroxide treated. Curve 513 shows the gel elasticity for the same dispersion when 10 mg/ml of PEG physical fiber-stabilizing agent is added to the dispersion during formulation to final product where the preceding collagen solution was sodium hydroxide treated. Curve 522 shows the gel elasticity data for the same dispersion when 2.5 mg/ml of PEG physical fiber-stabilizing agent is added during formulation to final product. Thus, there is a preferred PEG content for a product, depending on the end use application for the product. In the case of a non-crosslinked, injectable collagen dispersion for use in soft tissue augmentation, such as Zyderm®, the PEG content of the dispersion should range from about 1 mg/ml to about 4 mg/ml, preferably from about 2 mg/ml to about 4 mg/ml, and most preferably from about 2.4 mg/ml to 2.6 mg/ml. This presumes a PEG molecular weight of about 3 to 3.5 kD. One skilled in the art, with minimal experimentation can determine an optimized PEG content for particular product, depending on the PEG molecular weight and the end use application.

Figure 6A:
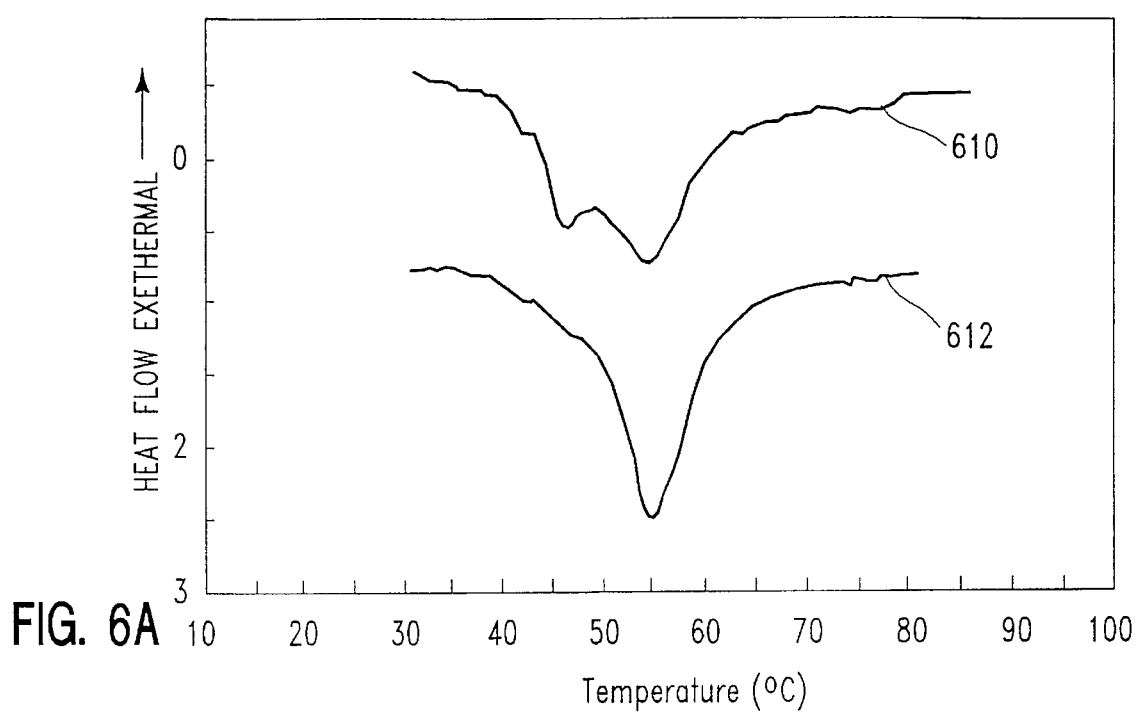
FIG. 6A shows the DSC thermogram for a dispersion containing 35 mg/ml of collagen, prepared from a sodium hydroxide-treated collagen solution. In one instance, the collagen fibers were formulated to final product with no fiber-stabilizing agent present; in the other instance a physical fiber-stabilizing agent (PEG) was present.
Figure 6B:
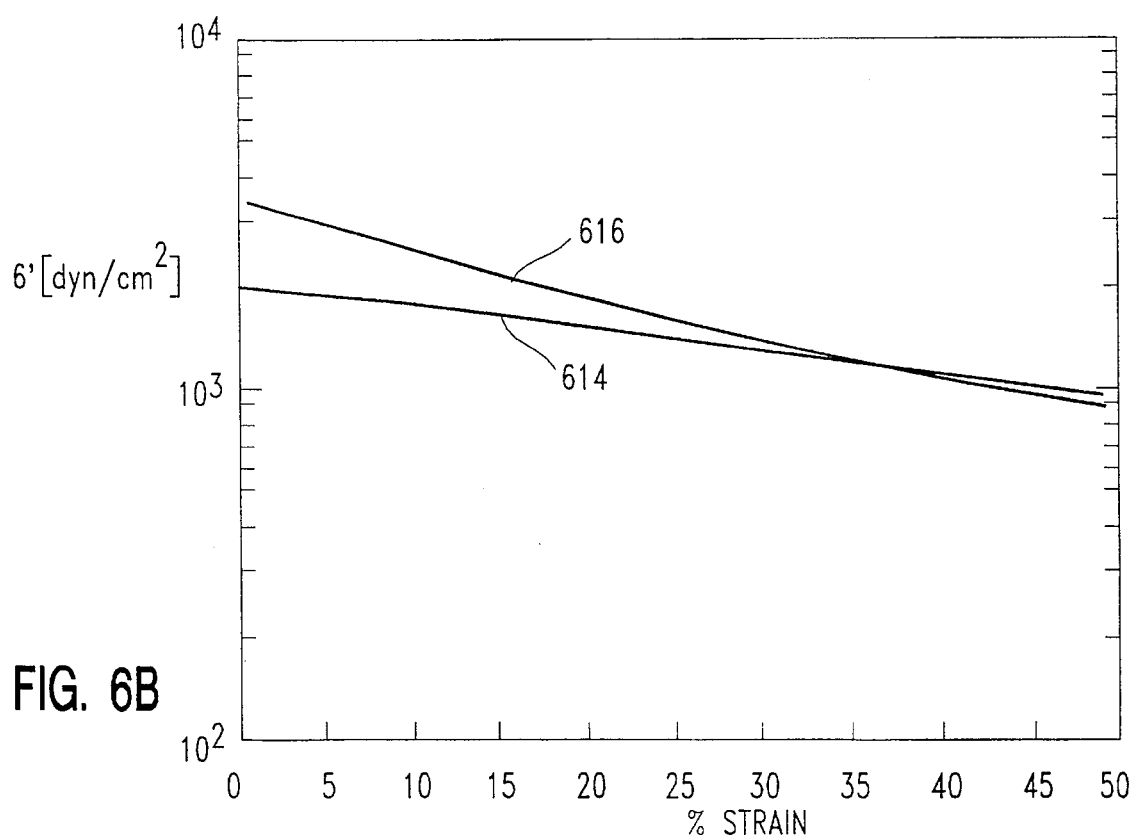
FIG. 6B shows the rheological characteristics, measured at 20° C. and 1 rad/sec for a dispersion of collagen fibers containing 35 mg/ml of collagen corresponding with the DSC curves are illustrated in FIG. 6A.

Further investigation indicated that addition of PEG as a stabilizing-agent during final formulation at a concentration providing about 2.5 mg/ml in the final formulation provided sufficient stabilization of the collagen fibers to meet normal Zyderm® requirements for fiber size population distribution, while only marginally affecting the rheological behavior of the product. FIG. 6A shows the DSC curves for collagen dispersions produced from a sodium hydroxide-treated solution of collagen and formulated to final product with lidocaine and salt; Curve 610 represents the absence of PEG from additives during formulation to final product, and Curve 612 shows the effect due to the presence of 2.5 mg/ml of PEG in the formulation. It is apparent that the 2.5 mg/ml of PEG fiber-stabilizing agent prevented the formation of a second, smaller sized fiber population. In addition, FIG. 6B shows the rheological properties for these materials, where storage modulus as a function of % strain for the control (non-sodium hydroxide treated collagen) formulation without PEG, shown in curve 614, is only marginally different from the curve 616 storage modulus as a function of % strain for the sodium hydroxide treated collagen formulated to final product with 2.5 mg/ml of PEG. The FIG. 6B storage modulus curves were generated at 20° C. and at a frequency of 1 rad/s.

One skilled in the art, in view of the present disclosure, can adjust the amount of fiber-stabilizing agent to provide the rheological properties desired in a given product while maintaining other physical properties desired in the collagen fibers themselves.

Example 4

Use of Crosslinking to Stabilize the Collagen Fiber for Formulation to Final Product. Chemical Process.

A. To determine whether crosslinking with trace amounts of a crosslinking agent would be useful in stabilizing the collagen fibers for formulation to final product, for example, glutaraldehyde was used as the crosslinking agent.

The procedure used to prepare a collagen suspension similar to Zyderm® was as follows:

The process described in Example 1A and illustrated in FIG. 1 was used to prepare sodium hydroxide treated CIS (NCIS).

The NCIS was used to prepare three different batches of material treated with trace amounts of glutaraldehyde. In each batch, 60 g of NCIS was placed in a 500 ml centrifuge bottle. The centrifuge bottle was placed in a 17° C. water bath. A 0.2M disodium phosphate buffer (adjusted to a pH of 11.2 using sodium hydroxide) was added in a ratio of 1:9 (buffer: NCIS), and the mixture was incubated for 8–12 hours. The bottles were shaken well and then a glutaraldehyde buffer was added at a concentration of about 0.5–2.0 mg glutaraldehyde per g of protein (essentially collagen) to provide a mixture having a pH of about 7–7.4, while stirring of the mixture was continued. In the first batch of material, the amount of glutaralehyde added was 0.5 mg glutaralehyde/g protein; 1.0 mg glutaraldehyde/g protein was used for the second batch; and 2.0 mg glutaraldehyde/g protein was used for the third batch. In each case, the mixture was permitted to incubate at 25±5° C. for a minimum period of 13 hours. For each batch, the contents of the beaker were transferred to a centrifuge bottle and the bottle was spun at about 9000 rpm for about 30 minutes in a Sorvall centrifuge (GS-3 rotor). The clear liquid was decanted from each bottle, leaving a pellet in the bottom of the bottle. Each pellet was transferred to a syringe, and mixing to obtain a homogeneous composition was accomplished by syringe-to-syringe exchange. The protein content of the homogeneous composition was about 40 to 80 mg/ml.

The computation of ingredients to be added to reach final product formulation was based on 35 mg/ml of protein in the final formulation. Lidocaine buffer (30 mg/ml lidocaine, 1.3M NaCl and 0.02M disodium phosphate at a pH of 6.3) was added to the homogeneous composition prepared above to produce a final formulation which contained 10% by volume of this buffer. The remainder of ingredients added was made up of 0.02M disodium phosphate buffer, pH 7.2. This mixture was mixed thoroughly by syringe to syringe exchange. The final formulation contained 35 mg/ml of protein, 0.13M sodium chloride, 0.02M sodium phosphate, and 3 mg/ml lidocaine in a water-based dispersion at a pH of 7.0–7.4.

Figure 7:
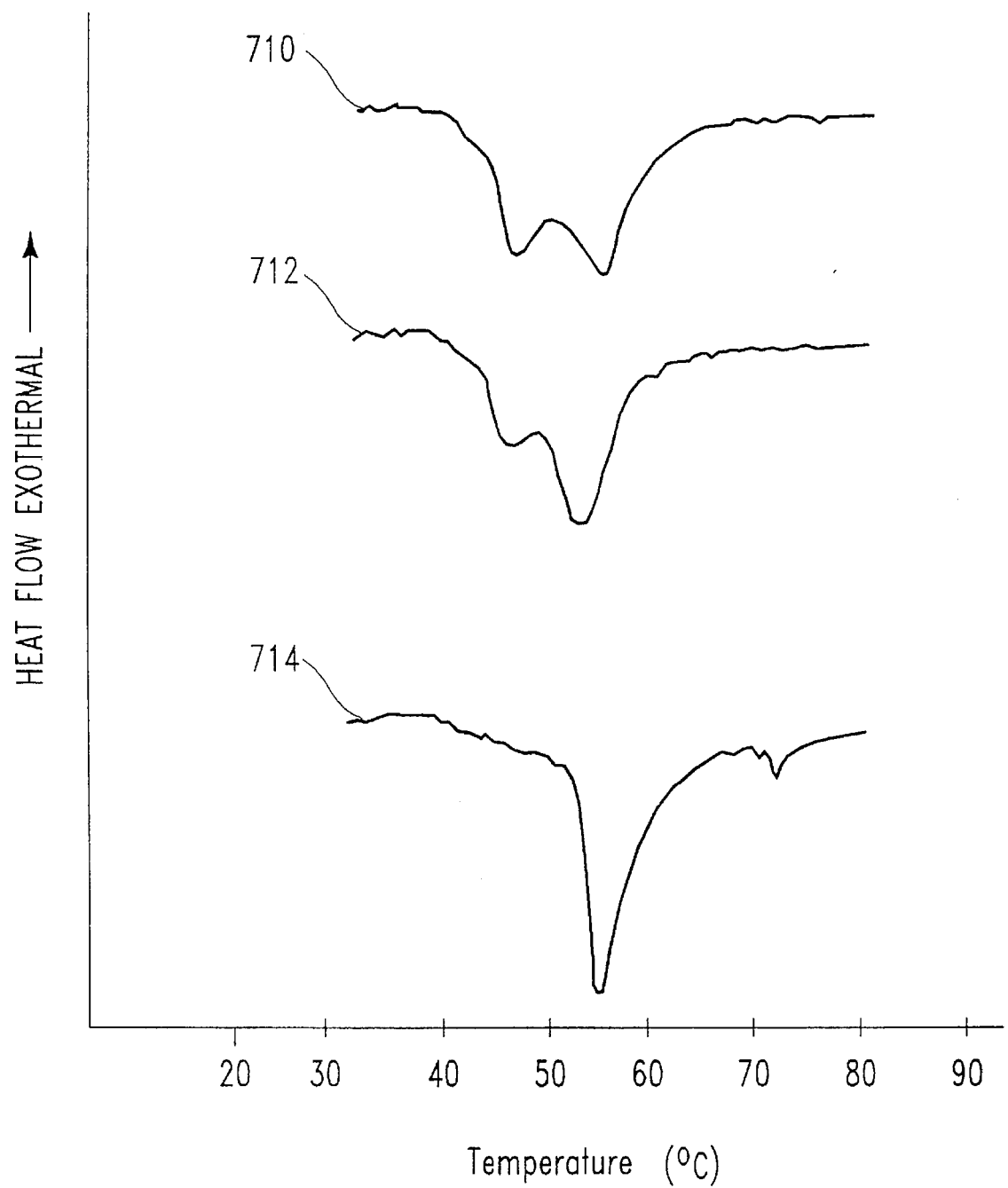
FIG. 7 provides the DSC thermograms for dispersions containing 35 mg/ml of collagen, prepared from a sodium hydroxide-treated collagen solution, where a differing amount of a chemical fiber-stabilizing agent (glutaraldehyde) was present in each instance.
Figure 8:
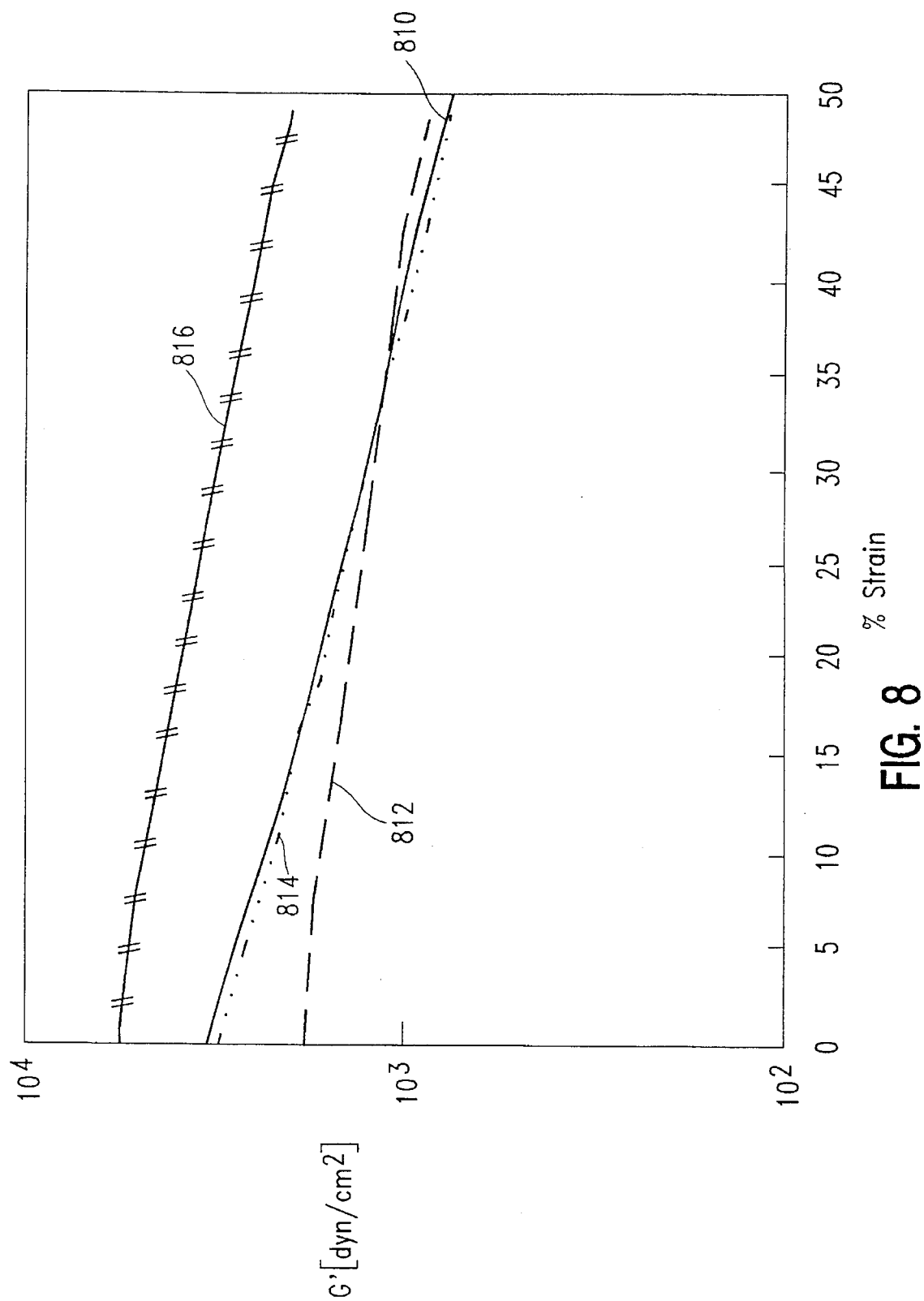
FIG. 8 shows the rheological characteristics, measured at 20° C.; and 1 rad/sec for formulated to final product under specific conditions. Curve 810 represents a dispersion of collagen fibers prepared from a non-sodium hydroxide-treated collagen solution (Control). Curve 812 represents a dispersion of collagen fibers prepared from a sodium hydroxide-treated solution without the presence of a fiber-stabilizing agent. Curve 814 represents collagen fibers prepared from a sodium hydroxide-treated solution where a physical fiber-stabilizing agent was present during formulation to final product. And, curves 816 represents a dispersion of collagen fibers prepared from sodium hydroxide-treated solutions, where a chemical fiber-stabilizing agent was present during formulation to final product.

The DSC profiles for the collagen dispersions from the three materials produced are shown in FIG. 7. FIG. 7, curve 710, shows the collagen fibers crosslinked using 0.5 mg glutaraldehyde/g protein; curve 712 shows the collagen dispersion DSC for fibers crosslinked using 1.0 mg glutaraldehyde/g protein; and curve 714 shows the collagen dispersion DSC for fibers crosslinked using 2.0 mg glutaraldehyde/g protein. It is readily apparent that crosslinking with 2.0 mg glutaraldehyde/g protein has stabilized the fibers in a manner which prevents destabilization upon formulation to final product. However, rheological measurements, illustrated in FIG. 8, showed that the collagen material behaves in a distinctly crosslinked manner even when such low concentrations of glutaraldehyde are used. Thus, the use of low concentrations of crosslinker, the chemical means of fiber stabilization, is not equivalent to the use of a physical fiber-stabilizing agent.

FIG. 8A shows the storage modulus as a function of % strain at 20° C. and 1 rad/sec for various collagen dispersions formulated to final product containing the amounts of lidocaine and salts previously described as present in the Zyderm® product. Curve 810 represents a collagen dispersion prepared without sodium hydroxide treatment (the control). Curve 812 represents a collagen dispersions prepared from sodium hydroxide treated solution, without use of any means of fiber stabilization during formulation to final product. Curve 814 represents a collagen dispersion prepared using sodium hydroxide treatment, with formulation to final product carried out in the presence of PEG, with the amount of PEG being such that the PEG content in the final product was 2.5 mg PEG/ml product. Curve 816 represents a collagen dispersion prepared using sodium hydroxide treatment and crosslinked with 1.0 mg glutaraldehyde/g protein just prior to formulation to final product.

It is readily apparent from FIG. 8 that the use of the physical fiber-stabilizing agent, PEG, during formulation to final product, to stabilize collagen fibers produced from a sodium hydroxide-treated solution, results in stabilized fibers which have theological properties very closely approaching those of collagen fibers produced from a solution which has not been treated with sodium hydroxide (the control). The use of a chemical means, i.e. a crosslinker, glutaraldehyde, just prior to formulation to final product, to stabilize the collagen fibers produced from a sodium hydroxide-treated solution, results in stabilized fibers whose fiber size population is not affected by formulation to final product; however, the theological properties of the fibers and the product produced therefrom will be different from the control. In some product applications, the chemically stabilized, crosslinked collagen fibers offer advantages and in other applications, the physically stabilized collagen fibers offer advantages.

B. In a single trial, glutaraldehyde was added to a collagen solution (NCIS), ie. after treatment of the solution with sodium hydroxide, but before precipitation (to fibers) and formulation to final product. 1.0 mg glutaraldehyde per g of collagen was used. The DSC curve of a collagen dispersion formulated to final product using the collagen from this trial (where no further glutaraldehyde was added upon formulation to final product) indicated that the collagen fibers had not been stabilized. Further investigation is to be carried out related to addition of a chemical stabilizing agent simultaneously with sodium hydroxide treatment of collagen solutions.

There are a number of crosslinkers which can be used to chemically stabilize the collagen fibers. Such crosslinkers include, but are not limited to, glutaraldehyde, hexamethyl diisocyanate, dimethyl suberimidate, carbimide, and activated polyethylene glycol. The most preferred are those which are biologically compatible. There are numerous derivatives of PEG which are biologically compatible and which have activated functional sites along the polymer chain or at the ends of the polymer chain which can be used to crosslink collagen. In particular, polyethylene glycol is modified to provide functional groups so that covalent bonding can occur between the activated PEG and the primary amino groups on a collagen molecule. The term PEG, as used in describing these activated materials, represents polymers having the repeating structure $(OCH_2CH_2)_n$. The activated PEGS preferred in the present invention include PEG succinimidyl glutarate, having a succinimidyl glutarate group

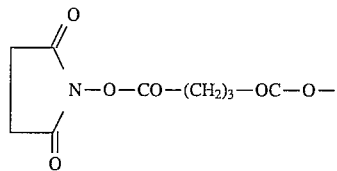

at least at two sites on the PEG molecule; PEG succinimidyl, having a succinimidyl group

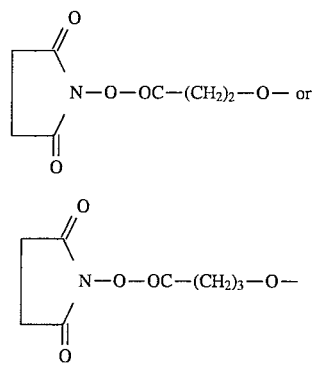

at least at two sites of the PEG molecule; PEG succinimidyl carbonate, having a succinimidyl carbonate group

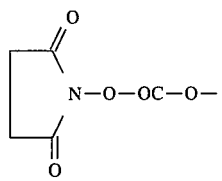

at least at two sites on the PEG molecule; PEG propion aidehyde, having an OHC—(CH$_2$)$_2$—O— functional group at least at two sites on the PEG molecule; and PEG glycidyl ether, having an O—CH$_2$—CH—CH$_2$—O— functional group at least at two sites on the PEG molecule.

One skilled in the an will recognize other biocompatible crosslinkers which can readily be used in the stabilization of collagen fibers.

The above-described preferred embodiments of the present invention are not intended to limit the scope of the present invention, as demonstrated by the claims which follow, as one skilled in the art can, with minimal experimentation, extend the disclosed concepts of the invention to the claimed scope of the invention.

What is claimed is:

1. An improved dispersion of collagen fibers prepared from a solution or a dispersion of collagen, said collagen having been treated with a sodium hydroxide to inactivate infectious agents and said collagen fibers having been destabilized as a result of treatment with said sodium hydroxide, wherein the improvement comprises said collagen fibers having been stabilized by a physical fiber-stabilizing agent, said agent comprising a polymeric material capable of causing collagen fibers to precipitate from solution.

2. The dispersion of stabilized collagen fibers of claim 1, wherein said polymeric material is water soluble or water miscible.

3. The dispersion of stabilized collagen fibers of claim 2, wherein said water soluble or water miscible polymeric material is selected from the group consisting of: polyvinyl alcohol, polyethylene oxide, polyvinylpyrrolidone, polyacrylamide, polyethylene glycol, polypropylene glycol, polyvinyl methyl ether, maleic anhydride copolymers, hydroxyethyl starches, methyl cellulose, hydroxymethyl cellulose, hydroxyethyl cellulose, hydroxypropyl cellulose, agarose, dextrins, dextrans, pectins and alginates.

4. The dispersion of stabilized collagen fibers of claim 2, wherein said water soluble or water miscible polymeric material is biocompatible.

5. The dispersion of stabilized collagen fibers of claim 4, wherein said water soluble or water miscible polymeric material is selected from the group consisting of polyethylene glycols and derivatives thereof.

6. The dispersion of stabilized collagen fibers of claim 5, wherein said water soluble or water miscible polymeric material is a polyethylene glycol having a molecular weight ranging from about 200 to about 20,000.

7. The dispersion of stabilized collagen fibers of claim 6, wherein said polyethylene glycol has a molecular weight ranging from about 200 to about 8,000.

8. An improved dispersion of collagen fibers prepared from a solution or a dispersion of collagen, said collagen having been treated with a sodium hydroxide to inactivate infectious agents and said collagen fibers having been destabilized as a result of treatment with said sodium hydroxide wherein the improvement comprises said collagen fibers having been stabilized by a chemical fiber-stabilizing agent, wherein said agent comprises a crosslinker reacted with said collagen fiber either prior to or subsequent to the treatment of said collagen solution or dispersion by said sodium hydroxide.

9. The dispersion of claim 8, wherein said crosslinker is reacted with said collagen fibers subsequent to the treatment of said solution or dispersion.

10. The dispersion of stabilized collagen fibers of claim 8 or claim 9, wherein said crosslinker is selected from the group consisting of glutaraldehyde, hexamethyl diisocyanate, dimethyl suberimidate, carbodiimide and activated polyethylene glycol.

11. The dispersion of stabilized collagen fibers of claim 8 or claim 9, wherein said crosslinker is biocompatible.

12. The dispersion of stabilized collagen fibers of claim 11, wherein said biocompatible crosslinker is an activated polyethylene glycol.

13. The dispersion of stabilized collagen fibers of claim 12, wherein said activated polyethylene glycol is selected from the group consisting of polyethylene glycol succinimidyl glutarate, polyethylene glycol succinimidyl, polyethylene glycol succinimidyl carbonate, polyethylene glycol propion aldehyde and polyethylene glycol glycidyl ether, wherein at least two active sites are present on each polyethylene glycol molecule prior to crosslinking with collagen fibers of said collagen dispersion.

14. In a method for preparing a dispersion of collagen fibers from a solution or a dispersion of collagen wherein said collagen has been treated with a sodium hydroxide to inactivate infectious agents and wherein said collagen fibers have been destabilized as a result of treatment with said sodium hydroxide, the improvement comprising stabilizing said collagen fibers subsequent to said treatment by reacting said collagen fibers with a physical fiber-stabilizing agent, said agent comprising a polymeric material capable of causing collagen fibers to precipitate from solution.

15. The method of claim 14, wherein said polymeric material is water soluble or water miscible.

16. The method of claim 15, wherein said water soluble or water miscible polymeric material is selected from the group consisting of polyvinyl alcohol, polyethylene oxide, polyvinylpyrrolidone, polyacrylamide, polyethylene glycol, polypropylene glycol, polyvinyl methyl ether, maleic anhydride copolymers, hydroxyethyl starches, methyl cellulose, hydroxymethyl cellulose, hydroxyethyl cellulose, hydroxypropyl cellulose, agarose, dextrins, dextrans, pectins and alginates.

17. The method of claim 15, wherein said water soluble or water miscible polymeric material is biocompatible.

18. The method of claim 17, wherein said biocompatible polymeric material is selected from the group consisting of polyethylene glycols and derivatives thereof.

19. The method of claim 18, wherein said water soluble or water miscible polymeric material is a polyethylene glycol having a molecular weight ranging from about 200 to about 20,000.

20. The method of claim 19, wherein said water soluble or water miscible polymeric material is a polyethylene glycol having a molecular weight ranging from about 1,000 to about 6,000.

21. The method of claim 20, wherein the concentration of said polyethylene glycol ranges from about 2.3 mg/ml to about 2.6 mg/ml and the concentration of said collagen fiber ranges from about 10 mg/ml to about 100 mg/ml.

22. The method of claim 21, wherein the concentration of polyethylene glycol ranges from about 2.3 mg/ml to about 2.6 mg/ml and the concentration of said collagen fiber ranges from about 10 to about 50 mg/ml.

23. In a method for preparing a dispersion of collagen fibers from a solution or a dispersion of collagen wherein said collagen has been treated with a sodium hydroxide to inactivate infectious agents and wherein said collagen fibers have been destabilized as a result of treatment with said sodium hydroxide, the improvement comprising crosslinking said collagen fibers by reacting said collagen fibers with a chemical fiber-stabilizing agent prior to or subsequent to said treatment with a sodium hydroxide of said solution or dispersion containing said collagen fibers.

24. The method of claim 23, wherein said crosslinking is accomplished using a biocompatible chemical fiber-stabilizing agent.

25. The method of claim 24 wherein said chemical fiber-stabilizing agent is an activated polyethylene glycol.

26. The method of claim 23, wherein said crosslinking is carried out subsequent to said treatment.

27. The method of claim 26, wherein said chemical fiber-stabilizing agent is glutaraldehyde.

28. The method of claim 27, wherein the concentration ratio of said glutaraldehyde to said collagen fiber ranges from about 0.0005:1 to about 0.02:1.

29. The method of claim 23 or claim 26, wherein said chemical fiber-stabilizing agent is selected from the group consisting of glutaraldehyde, hexamethyl diisocyanate, dimethyl suberimidate, carbodiimide and activated polyethyleneglycol.

* * * * *